United States Patent [19]
Brocks et al.

[11] Patent Number: 4,968,670
[45] Date of Patent: Nov. 6, 1990

[54] PYRIDINE-2,4- AND 2,5-DICARBOXYLIC ACID DERIVATIVES, A PROCESS FOR THEIR PREPARATION, THE USE THEREOF, AND MEDICAMENTS BASED ON THESE COMPOUNDS

[75] Inventors: Dietrich Brocks, Wiesbaden; Harald Burghard, Schmitten; Volkmar Günzler, Marburg-Cappel; Hartmut Hanauske-Abel, Dexheim, all of Fed. Rep. of Germany

[73] Assignee: Hoechst Aktiengesellschaft, Frankfurt am Main, Fed. Rep. of Germany

[21] Appl. No.: 153,440

[22] Filed: Feb. 8, 1988

[30] Foreign Application Priority Data

Feb. 10, 1987 [DE] Fed. Rep. of Germany ....... 3703962

[51] Int. Cl.$^5$ ..................... A01K 31/44; C07D 213/81
[52] U.S. Cl. ...................................... 514/18; 514/354; 530/331; 546/323
[58] Field of Search ....................... 546/323; 530/331; 514/18, 354

[56] References Cited

FOREIGN PATENT DOCUMENTS 3432094 3/1986 Fed. Rep. of Germany ...... 546/290
85/6646 8/1985 South Africa ...................... 546/290

OTHER PUBLICATIONS

W. Muller et al., FEBS Lett. 90 (1978), 218; Immunobiology 155 (1978) 47.
A. Hubbuch, Schutzgruppen in der Peptidsynthese (Teil 1): Schutzgruppentaktik, Amino- und Carboxyl-Schutzgrupen, Kontakte 3/79, pp. 15 & 19 et seq.
Houben-Weyl, Methoden der Organischen Chemie (Methods of Organic Chemistry), vol. E5, pp. 496–504, 4th Ed., 1985.
Houben-Weyl, Methoden der Organischen Chemie, vol. XV/2, pp. 103–111, 4th Ed., Georg Thieme Verlag, Stuttgart, 1974.
Organikum, Organisch Chemisches Grundpraktikum (Basic Techniques of Organic Chemistry), 15th Ed., VEB Deutscher Verlag der Wissenschaften, 1976, pp. 595 et seq.
Houben-Weyl, Methoden der Organischen Chemie, vol. XV/2, pp. 169–183, 4th Ed., 1974, Georg Thieme Verlag Stuttgart.
W. Muller et al., FEBS Letters, vol. 90, 1978, p. 218.
K. Majamaa et al., Eur. J. Biochem., vol. 138, 1984, pp. 239–245.
V. Gunzler et al., Collagen and Rel. Research, vol. 3, p. 71, 1983.
The Liver, C. Rouiller, vol. 2, pp. 335–476, New York, Academic Press, 1964.
Talma et al., Journal of the American Chemical Society, vol. 107, pp. 3981–3997 (1985).
Atwell et al., Journal of Medicinal Chemistry, vol. 10, No. 4, pp. 706–713 (Jul. 1967).

Primary Examiner—John M. Ford
Assistant Examiner—J. Richter
Attorney, Agent, or Firm—Finnegan, Henderson, Farabow, Garrett, and Dunner

[57] ABSTRACT

Pyridine-2,4- and 2,5-dicarboxylic acid derivatives, a process for their preparation, the use thereof, and medicaments based on these compounds.

The invention relates to pyridine-2,4- and -2,5-dicarboxylic acid derivatives of the formula I

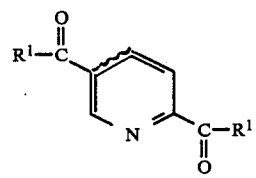

(I)

in which $R^1$, $R^2$ and X have the indicated meanings, to a process for the preparation of these compounds, and to their use, in particular in medicaments for influencing the metabolism of collagen and collagen-like substances and the biosynthesis of C1q.

7 Claims, No Drawings

PYRIDINE-2,4- AND 2,5-DICARBOXYLIC ACID DERIVATIVES, A PROCESS FOR THEIR PREPARATION, THE USE THEREOF, AND MEDICAMENTS BASED ON THESE COMPOUNDS

SPECIFICATION

Compounds which inhibit proline and lysine hydroxylase bring about very selective inhibition of collagen biosynthesis by influencing the collagen-specific hydroxylase reactions. In the course of these, protein-bound proline or lysine is hydroxylated by the enzymes proline or lysine hydroxylase, respectively. If this reaction is suppressed by inhibitors there results a collagen molecule which is under-hydroxylated, is unable to function and can be released from the cell into the extracellular space only in a small amount. The under-hydroxylated collagen cannot, moreover, be incorporated in the collagen matrix, and is very readily broken down by proteolysis. As a consequence of these effects there is a reduction in the total amount of collagen undergoing extracellular deposition.

It is known that inhibition of proline hydroxylase by known inhibitors, such as $\alpha,\alpha$-dipyridyl, results in inhibition of C1q biosynthesis by macrophages (W. Müller et al., FEBS Lett. 90 (1978), 218; Immunobiology 155 (1978) 47). This results in the classic pathway of complement activation becoming inoperative. Hence, inhibitors of proline hydroxylase also act as immunosuppressants, for example in immune complex diseases.

It is known that proline hydroxylase is effectively inhibited by pyridine-2,4- and -2,5-dicarboxylic acid (K. Mayama et al., Eur. J. Biochem. 138 (1984) 239–245). However, in cell culture, these compounds are effective inhibitors only in very high concentrations (V. Günsler et al., Collagen and Rel. Research 3, 71 1983). DE-A No. 34 32 094 describes pyridine-2,4- and -2,5-dicarboxylic diesters having 1–6 carbon atoms in the ester alkyl moiety as medicaments for the inhibition of proline and lysine hydroxylase.

However, these low-alkyl diesters have the disadvantage that they are too rapidly cleaved to the acids in the body and do not reach their site of action in the cell in sufficiently high concentration and thus are relatively poorly suited for any administration as medicaments.

It has now been found, surprisingly, that the $\alpha$-amino acid, $\alpha$-amino acid ester, di- or tripeptide derivatives of pyridine-2,4- and -2,5-dicarboxylic acid are excellent inhibitors of collagen biosynthesis in animal models.

The actual active substance, the pyridine-2,4- or -2,5-dicarboxylic acid, is produced in the cell only after hydrolysis of the $\alpha$-amino acid, $\alpha$-amino acid ester, di- or tripeptide derivatives. The $\alpha$-amino acid, $\alpha$-amino acid ester, di- or tripeptide derivatives can, by reason of their relatively high lipophilicity and the fact that, surprisingly, they are only very slowly hydrolyzed during transport, be transported into the cells. Only here is the actual active substance, pyridine-2,4- or -2,5-dicarboxylic acid, liberated.

Thus the invention relates to:
1. Pyridine-2,4- or -2,5-dicarboxylic acid derivatives of the formula I,

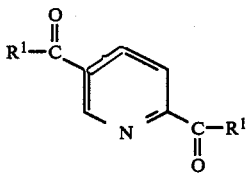

in which
R$^1$ denotes an $\alpha$-amino acid or $\alpha$-amino acid alkyl ester or $\alpha$-amino acid amide or $\alpha$-amino acid alkyl- or dialkylamide which is bonded via the N terminus and in which the said alkyl radicals have 1 to 4 carbon atoms and are optionally mono-substituted by phenyl, and in which the C$_3$- and C$_4$-alkyl radicals can also be branched, or
R$_1$ denotes di- or tripeptide which is bonded via the N-terminus,
and their physiologically tolerated salts.
2. Preferred pyridine-2,4- or -2,5-dicarboxylic acid derivatives of the formula I are those in which
R$^1$ denotes $\alpha$-amino acid or $\alpha$-amino acid alkyl ester which is bonded via the N terminus and in which the alkyl radical has 1 to 3 carbon atoms and is optionally monosubstituted by phenyl and in which the C$_3$-alkyl radical can also be branched,
and their physiologically tolerated salts.

The invention also relates to a process for the preparation of pyridine-2,4- or -2,5-dicarboxylic acid derivatives of the formula I, which comprises reaction of a compound of the formula II

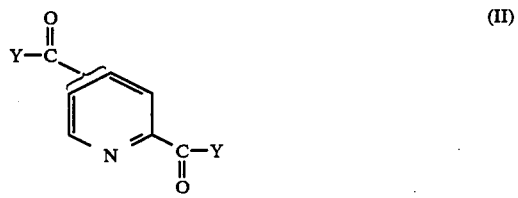

with a compound of the formula III

in which
R$^1$ has the meanings indicated for formula I, and Y is halogen or hydroxyl or, together with the carbonyl group, forms an active ester or an anhydride, and in which, in the case where R$^1$ is a di- or tripeptide which is bonded via the N terminus or an $\alpha$-amino acid which is bonded via the N terminus, the free carboxyl group(s) which is (are) present is(are) optionally protected, and in which this(these) protective group(s) which is(are) optionally present is(are) eliminated after the reaction by hydrolysis or hydrogenolysis to form the free carboxyl group(s), and conversion of the reaction products, where appropriate, into their physiologically tolerated salts.

The preparation of compounds of the formula I and the preparation of the starting substances required for this—where they cannot be bought—are described in detail hereinafter.

Suitable temporary carboxyl protective groups are ester protective groups as are also used in peptide synthesis (compare, for example, Kontakte Merck 3/79, pages 15 and 19 et seq.).

The methyl, benzyl or tert.-butyl ester is often used, as are ONbzl, OMbzl and OPic. The elimination depends on the protective group and is carried out by acid or alkaline hydrolysis or by hydrogenation in the presence of a transition metal catalyst (Houben-Weyl, Methoden der Organischen Chemie (Methods of Organic Chemistry), Volume E5, pages 496–504, fourth edition, 1985).

The compounds according to the invention are prepared most straightforwardly by mixing the two components, the pyridine derivative of the formula (II) and the α-amino acid or the α-amino acid derivative of the formula (III), in equimolar amounts or with an up to about 5-fold excess of III, and reacting them at temperatures between −30 and 150° C., preferably at 20° to 100° C., until the reaction is complete. The completion of the reaction can be determined by thin-layer chromatography (TLC checks). A variant of this process comprises carrying it out in a suitable solvent, such as diethyl ether or dimethoxyethane or tetrahydrofuran, chlorinated hydrocarbons such as methylene chloride, chloroform, tri- or tetrachloroethylene, benzene, toluene or polar solvents such as dimethylformamide or acetone or dimethyl sulfoxide. In this case too it is possible to use an excess of α-amino acid or α-amino acid derivative of the formula (III), which can be up to about 5 times these amounts. The reaction temperatures in this case are between room temperature and the boiling point of the solvent, particular preference being given to temperatures in the range from room temperature to 130° C.

Where appropriate, the reaction can also be carried out in the presence of bases. Suitable additional bases are inorganic acid traps such as carbonates or bicarbonates, for example sodium or potassium carbonate or sodium or potassium bicarbonate, or organic acid traps such as tertiary amines, such as triethylamine, tributylamine, ethyldiisopropylamine or heterocyclic amines such as N-alkylmorpholine, pyridine, quinoline or dialkylanilines.

The reaction of the compounds of the formula (II) with the α-amino acids or α-amino acid derivatives of the formula (III) is preferably carried out with the addition of a water-eliminating agent such as dialkylcarbodiimide in which the alkyl radicals have 1 to 8 carbon atoms and which, in the case of the $C_3$–$C_8$ compounds, can also be branched or cyclic; dicyclohexylcarbodiimide is preferably used. An appropriate method is described in Houbey-Weyl, Vol. XV/2, pages 103–111, Methoden der Organischen Chemie, 4th edition, Georg Thieme Verlag, Stuttgart, 1974.

Where appropriate, the products can be worked up by, for example, extraction or chromatography, for example on silica gel. The isolated product can be recrystallized and, where appropriate, reacted with a suitable acid to give a physiologically tolerated salt. Examples of suitable acids are:

mineral acids such as hydrochloric and hydrobromic acid, and sulfuric, phosphoric, nitric or perchloric acid, or organic acids such as formic, acetic, propionic, succinic, glycolic, lactic, malic, tartaric, citric, maleic, fumaric, phenylacetic, benzoic, methanesulfonic, toluenesulfonic, oxalic, 4-aminobenzoic, naphthalene-1,5-disulfonic or ascorbic acid.

The starting compounds of the formula (II) are obtained, for example, by reaction of pyridine-2,4- or -2,5-dicarboxylic acid (II, Y=hydroxyl) to give the corresponding pyridine-2,4- or -2,5-dicarbonyl halide, preferably chloride (II, Y=halogen) (by processes known from the literature, for example Organikum, Organisch Chemisches Grundpraktikum (Basic Techniques of Organic Chemistry), 15th edition, VEB Deutscher Verlag der Wissenschaften, 1976, pages 595 et seq.), which is then reacted with a suitable alcohol, for example paranitrobenzyl alcohol, to give the corresponding active ester (II, Y=active ester). It is likewise possible initially to convert the pyridine-2,4- or -2,5-dicarboxylic acid, with the addition of a suitable carboxylic acid or carboxylic ester such as ethyl chloroformate, into a mixed anhydride (II, Y=anhydride), which is then reacted with the α-amino acids or α-amino acid derivatives to give the products according to the invention. An appropriate method is described, for example, in Houben-Weyl, Methoden der Organischen Chemie, Volume XV/2, pages 169–183, 4th edition, 1974, Georg Thieme Verlag Stuttgart.

The compounds of the formula I, according to the invention, have valuable pharmacological properties and display, in particular, efficacy as inhibitors of proline and lysine hydroxylase, as fibrosuppressants and immunosuppressants.

The activity of fibrogenase can be determined by radioimmunological determination of the N-terminal propeptide of collagen type III or the N- or C-terminal crosslinking domain of collagen type IV (7s collagen or type IV collagen $NC_1$) in the serum.

For this purpose, the concentrations of hydroxyproline, procollagen III peptide, 7s collagen and type IV collagen $NC_1$ have been measured in the livers of (a) untreated rats (controls)
(b) rats administered with carbon tetrachloride ($CCl_4$ controls)
(c) rats administered first with $CCl_4$ and then with a compound according to the invention (this assay method is described by Rouiller, C., experimental toxic injury of the liver; in The Liver, C. Rouiller, Vol. 2, pages 335–476, New York, Academic Press, 1964).

The pharmacological efficacy of the substances according to the invention has been investigated; this revealed a distinct inhibition of proline and lysine hydroxylase.

The compounds of the formula I can be used as medicaments in the form of pharmaceutical products which contain them, where appropriate together with tolerated pharmaceutical vehicles. The compounds can be used as medicines, for example in the form of pharmaceutical products which contain these compounds mixed with an organic or inorganic pharmaceutical vehicle which is suitable for enteral, percutaneous or parenteral administration, such as, for example, water, gum arabic, gelatin, lactose, starch, magnesium stearate, talc, vegetable oils, polyalkylene glycols, Vaseline etc. The pharmaceutical products can be in solid form, for example as tablets, coated tablets, suppositories or capsules; in semi solid form, for example as ointments, or in liquid form, for example as solutions, supensions or emulsions. Where appropriate, they are sterilized and/or contain auxiliaries such as preservatives, stabilizers, wetting agents or emulsifiers, salts to alter the osmotic pressure or buffers. They can also contain other therapeutically active substances in addition. The invention is explained in detail hereinafter by means of examples:

EXAMPLES

1. Bis(1-methoxycarbonylethyl)amide of pyridine-2,4-dicarboxylic acid 1.02 g of di(4-nitrophenyl) pyridine-2,4-dicarboxylate are dissolved in 25 ml of dry dimethylformamide, and 0.69 g of alanine methyl ester hydrochloride and 1.15 ml of triethylamine are added. The mixture is then stirred at room temperature for 2 hours and left to stand overnight. The reaction mixture is taken up in diethyl ether, and the solution is washed 5 times with water. The organic phase is dried with sodium sulfate, and the solvent is removed. The residue is chromatographed on silica gel using ethyl acetate as eluant. The oily residue is crystallized with pentane/ether.

Melting point 96° C.; yield 80 mg

2. Bis(1-benzyloxycarbonyl-2-phenylethyl)amide of pyridine-2,4-dicarboxylic acid 2.5 g of di(4-nitrophenyl) pyridine-2,4-dicarboxylate are dissolved in 70 ml of dry dimethylformamide, and 3.56 g of phenylalanine benzyl ester hydrochloride and 7.0 ml of triethylamine are added. The mixture is then stirred at room temperature for 3 hours and left to stand overnight. The reaction mixture is taken up in diethyl ether, and the solution is washed 5 times with water. The product crystallizes on tipping out and is filtered off with suction.

Melting point 104° C.; yield 3.46 g

3. Bis(1-benzyloxycarbonyl-3-methylbutyl)amide of pyridine-2,4-dicarboxylic acid 1.02 g of di(4-nitrophenyl) pyridine-2,4-dicarboxylate are dissolved in 50 ml of dry dimethylformamide, and 2.9 g of leucine benzyl ester tosylate and 2 ml of triethylamine are added. The mixture is then stirred at room temperature for 3 hours and left to stand overnight. The reaction mixture is taken up in diethyl ether, and the solution is washed 5 times with water. The organic phase is dried with sodium sulfate, and the solvent is removed. The residue is chromatographed on silica gel using ethyl acetate as eluant. The oily residue is crystallized with pentane/ether.

Melting point 82° C.; yield 1.14 mg

4. Bis(1-benzyloxycarbonyl ether)amide of pyridine-2,4-dicarboxylic acid 0.87 g of di(4-nitrophenyl) pyridine-2,4-dicarboxylate is dissolved in 30 ml of dry dimethylformamide, and 1.5 g of alanine benzyl ester tosylate and 1 ml of triethylamine are added. The mixture is then stirred at room temperature for 2 hours and left to stand overnight. The reaction mixture is taken up in diethyl ether, and the solution is washed 5 times with water. The organic phase is dried with sodium sulfate, and the solvent is removed. The residue is chromatographed on silica gel using toluene/ethyl acetate in the ratio 4:1 as eluant. The oily residue is stirred with ether, and the product is filtered off with suction.

Melting point 103° C.; yield 0.5 g

5. Bis(1-benzyloxycarbonyl-2-(3-indolyl)ethyl)amide of pyridine-2,4-dicarboxylic acid 1.02 g of di(4-nitrophenyl) pyridine-2,4-dicarboxylate are dissolved in 30 ml of dry dimethylformamide, and 1.4 g of tryptophan benzyl ester and 0.45 ml of triethylamine are added. The mixture is then stirred at room temperature for 3 hours and left to stand overnight. The reaction mixture is chromatographed on silica gel using a 4:1 mixture of toluene and ethyl acetate as eluant. The residue is stirred with diisopropyl ether, and the product is filtered off with suction.

Melting point 81° C.; yield 0.9 g

6. Bis(1-methoxycarbonyl-3-methylbutyl)amide of pyridine2,4-dicarboxylic acid 1.5 g of bis(4-nitrophenyl) pyridine-2,4-dicarboxylate are reacted with 1.3 g of leucine methyl ester hydrochloride in analogy to Example 1. The reaction mixture is worked up as described in Example 1 and chromatographed on silica gel using a 4:1 mixture of toluene/ethyl acetate. After removal of the solvent in vacuo, the residue is stirred with petroleum ether, and the product is filtered off with suction.

Melting point 94° C; yield 1.0 g

7. Bis(1-benzyloxycarbonyl-3-methylpropyl)amide of pyridine-2,5-dicarboxylic acid 1.02 g of bis(4-nitrophenyl) pyridine-2,5-dicarboxylate are reacted with 1.97 g of L-leucine benzyl ester toluene-4-sulfonate, and worked up, in analogy to Example 1. The product is chromatographed on silica gel using a 2:1 mixture of toluene and ethyl acetate. After removal of the solvent in vacuo, the product is stirred with diisopropyl ether and filtered off with suction.

Melting point 76° C.; yield 0.38 g

8. Bis(1-benzyloxycarbonyl-2-phenylethyl) amide of pyridine-2,5-dicarboxylic acid 1.02 g of bis(4-nitrophenyl) pyridine-2,5-dicarboxylate are reacted with 1.5 g of phenylalanine benzyl ester hydrochloride, and worked up, in analogy to Example 1. The product is chromatographed on silica gel using a 4:1 mixture of toluene and ethyl acetate. After removal of the solvent in vacuo, the product is stirred with diethyl ether, filtered off with suction and recrystallized from a little ethyl acetate.

Melting point 142° C.; yield 0.9 g

9. Bis(1-benzyloxycarbonyl-2-(3-indolyl)ethyl)amide of pyridine-2,5-dicarboxylic acid 1.02 g of bis(4-nitrophenyl)pyridine-2,5-dicarboxylate are reacted with 1.4 g of tryptophan benzyl ester in analogy to Example 1. For the working up, the reaction mixture is taken up in diethyl ether, and the solution is washed several times with water. The organic phase is dried, the solvent is removed, and the residue is chromatographed once on silica gel using a 1.5:1 mixture of toluene and ethyl acetate and subsequently once again on silica gel using a 1:1 mixture of cyclohexane and ethyl acetate.

Melting point 92° C.; yield 0.3 g

We claim:

1. Pyridine-2,4- and -2,5-dicarboxylic acid derivatives of the formula I

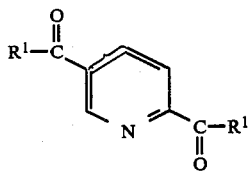

in which

R[1] denotes an α-amino acid or α-amino acid alkyl ester or α-amino acid amide or α-amino acid alkyl- or dialylamide which is bonded via the N-terminus and in which the said alkyl radicals have 1 to 4 carbon atoms and are optionally monosubstituted by phenyl, and in which the $C_3$- and $C_4$-alkyl radicals can also be branched, or R[1] denotes di- or tripeptide which is bonded via the N-terminus, and their physiologically tolerated salts.

2. Pyridine-2,4- or -2,5-dicarboxylic acid derivatives of the formula I as claimed in claim 1, in which R[1] denotes α-amino acid or α-amino acid alkyl ester which is bonded via the N-terminus and in which the alkyl radical has 1 to 3 carbon atoms and is optionally monosubstituted by phenyl and in which the $C_3$-alkyl radical can also be branched, and their physiologically tolerated salts.

3. A method for inhibiting proline and lysine hydroxylase in a mammal comprising administering a pharmaceutically effective amount of a compound of the formula I as claimed in claim 1.

4. A method for fibrosuppression and immunosuppression in a mammal comprising administering a pharmaceutically effective amount of a compound of the formula I as claimed in claim 1.

5. A method for influencing the metabolism of collagen and collagen-like substances and the biosynthesis of C1q in a mammal comprising administering a pharmaceutically effective amount of a compound of the formula I as claimed in claim 1.

6. A method for treating disturbance of the metabolism of collagen and collagen-like substances and the biosynthesis of C1q in a mammal comprising administering a pharmaceutically effective amount of a compound of the formula I as claimed in claim 1.

7. A pharmaceutical composition for the inhibition of proline and lysine hydroxylase in a mammal which comprises an effective amount for said inhibition of a compound of the formula I as claimed in claim 1 together with a pharmaceutically tolerated vehicle.

* * * * *